United States Patent [19]

Koch et al.

[11] Patent Number: 5,538,954
[45] Date of Patent: Jul. 23, 1996

[54] SALTS OF TETRACYCLINES

[75] Inventors: Torben Koch, Copenhagen; Hjarne Dyrsting, Virum, both of Denmark

[73] Assignee: A/S Dumex (Dumex Ltd.), Copenhagen, Denmark

[21] Appl. No.: 265,193

[22] Filed: Jun. 24, 1994

[51] Int. Cl.$^6$ .............................. A61K 31/70; C07H 5/00
[52] U.S. Cl. .................. 514/53; 536/1.11; 536/4.1; 536/123.13; 536/121; 536/122; 552/203
[58] Field of Search .............................. 536/1.1, 4.1, 121, 536/122; 514/53; 552/203

[56] References Cited

U.S. PATENT DOCUMENTS

| | | | |
|---|---|---|---|
| 3,200,149 | 8/1965 | Blackwood et al. | 552/203 |
| 3,432,489 | 3/1969 | Nitta et al. | 536/121 |
| 3,927,094 | 12/1975 | Villax | 552/203 |
| 5,143,934 | 9/1992 | Ladiing et al. | 514/396 |

FOREIGN PATENT DOCUMENTS

| | | |
|---|---|---|
| 0091409B1 | 2/1986 | European Pat. Off. . |
| 2088864 | 6/1982 | United Kingdom . |
| WO94/00476 | 1/1994 | WIPO . |

OTHER PUBLICATIONS

Richard S. Berger, MD.; "A Double–Blind, Multiple–Dose, Placebo–Controlled, Cross–Over Study to Compare the Incidence of Gastrointestinal Complaints in Healthy Subjects Given Doryx R and Vibramycin R"; *J. Clin. Pharmacol*; 28:367–370 (1988).

Joseph B. Bogardus; "Dissolution Rates of Doxycyline Free Base and Hydrochloride Salts"; *Journal of Pharmaceutical Sciences*; vol. 68; No. 9; pp. 1183–1184 (Sep. 1979).

Burke A. Cunha et al.; "Doxycyline"; *Therapeutic Drug Monitoring*; 4:115–135 (1982).

Georges Delpre, MD et al.; "Induction of Esophageal Injuries by Doxycycline and Other Pills"; *Digestive Diseases and Sciences*; vol. 34, No. 5; pp. 797–800 (May 1989).

Milo Gibaldi; "Pharmacokinetics of Absorption and Elimination of Doxycycline in Man"; *Chemotherapia*; vol. 12; No. 5; pp. 265–271 (1967).

A. Grahnen, Ph.D. et al.; "Effect of Increasing Gastric pH on the Relative Bioavailability of Doxycycline Carrageenate Tablets 100 MG (Kabi Pharmacia) in Comparison with Vibramycin®Novum Tablets 100 MG (Pfizer)"; *Final Report*; (Aug. 1991).

Anna–Stina Malmborg; "Bioavailability of Doxycycline Monohydrate"; *Chemotherapy*; 30:76–80 (1984).

Hideki Morikawa et al.; "Structural Analysis of the Amorphous Sodium Salt and Aluminium Hydroxide Salt of Sucrose Sulphate"; *J Chem. Soc.*; 77:629–639 (1981).

Renpei Nagashima, Ph. D.; "Mechanisms of Action of Sucralfate"; *J. of Clin. Gastroenterology*; 3 (suppl. 2):117–127 (1981).

Vu X. Nguyen et al.; "Effect of Oral Antacid Administration on the Pharmacokinetics of Intravenous Doxycycline"; *Antimicrob. Agents Chemother.*; vol. 33; No. 4; pp. 435–436 (Apr. 1989).

Kiyoshige Ochi et al.; "Crystalline Salts of Sucrose Octasulfate"; *Chem. Pharm. Bull.*; 28(2):638–641 (1980).

S. Saivin et al.; "Clinical Pharmacokinetics of Doxycyline and Minocycline"; *Clinical Pharmacokinetics*; 15:355–366 (1988).

M. Schach von Wittenau; "A Symposium on Doxycycline: Pharmacokinetics of Doxycycline"; *OPMSAZ*; 33:5–10 (1974).

M. J. Story et al.; "Doxycycline Tolerance Study: Incidence of Nausea after doxycycline administration to healthy volunteers: A comparison of 2 formulations (Doryx'vs vibramycin')"; *Eur. J. Clin. Pharmacol*; 40:419–421 (1991).

Desmond B. Williams et al.; "Absorption of Doxycycline from a Controlled Release Pellet Formulation: The Influence of Food on Bioavailability"; *Biopharmaceutics & Drug Disposition*; vol. 11; pp. 93–105 (1990).

*Primary Examiner*—Elli Peselev
*Attorney, Agent, or Firm*—Watov & Kipnes

[57] ABSTRACT

A salt of sucrose-octa-O-sulfonic acid and a tetracycline useful in inhibiting protein synthesis of bacteria.

15 Claims, 4 Drawing Sheets

SALTS OF TETRACYCLINES

FIELD OF THE INVENTION

The invention relates to new salts of tetracyclines, especially doxycycline, and a process for the preparation thereof. The invention also relates to novel pharmaceutical compositions containing the new salts and the uses of the new salts in medicine.

The new salts comprise sucrose-octa-O-sulphonic acid and a tetracycline antibiotic with doxycycline being preferred.

BACKGROUND OF THE INVENTION

For more than 50 years, the tetracyclines have been used as antibiotics. An especially valuable member of the tetracycline family is doxycycline. This broad-spectrum antibiotic was first synthesised in 1962 and marketed by Pfizer under the name Vibramycin®.

Doxycycline is available in several different salts: Doxycycline monohydrate, doxycycline hydrochloride (hyclate), doxycycline carrageenate, doxycycline calcium and doxycycline phosphate (fosfatex).

Doxycycline shares its mode of action with other tetracyclines: Inhibition of bacterial protein synthesis. The inhibition is established through inhibition of binding of aminoacyl-tRNA primarily to 70S ribosomes but also to 30S ribosomes. The inhibition only leads to a bacteriostatic effect of the tetracyclines including doxycycline. Tetracyclines are active against a broad range of both gram positive and gram negative bacteria, aerobes as well as anaerobes. In all cases examined, doxycycline was found as effective as tetracycline and for several bacteria even more effective than tetracycline (Cunha 1982). Bacterial resistance to tetracyclines are frequent both in vitro and in vivo, and the resistance is transferred by a plasmid. Due to the bacteriostatic effect of tetracyclines they usually can not be combined with other cell-cycle specific antimicrobial agents, as the resting cells do not change cell cycle.

Most tetracyclines are incompletely absorbed and their absorption is dependent on the concomitant food intake. Absorption of doxycycline is almost complete (73–95%) and independent of food intake (Saivin, 1988).

The pharmacokinetic parameters of the different salts (hyclate, monohydrate, carrageenate) of doxycycline do not significantly differ under standard conditions (Saivin 1988, Grahnen 1991) and several comparative studies are found in the literature.

Doxycycline undergoes enterohepatic recycling-as first suggested by Gibaldi 1967, and later confirmed in pharmacokinetic profiles obtained by Malmborg 1984 and Nguyen 1989. The secondary peak in serum concentration due to reabsorption occurs around 10 to 12 hours after administration. Not all reports on doxycycline pharmacokinetics note the secondary peak, this can either be due to the fact that few samples are collected around the time of the secondary peak or because the data presented is adjusted to a pharmacokinetic model, which does not take the enterohepatic recycling into account.

The relative long half life of doxycycline in combination with enterohepatic recycling leads to accumulation after multiple dosing of doxycycline. The terminal half life is up to 22 hours and therefore once a day dosage of doxycycline is possible (Schach von Wittenau 1974).

Two factors have been reported which influence the pharmacokinetics of doxycycline. The pH in the stomach (Grahnén 1991) and concomitant administration of oral antacids (Nguyen 1989).

An increased pH of the stomach (Bogardus 1979b) decreases the bioavailability of doxycycline monohydrate whereas doxycycline hyclate and doxycycline carrageenate dissociation and absorption are independent of pH.

The increased pH in the stomach after omeprazole administration is expected to slow down the dissolution of doxycycline monohydrate and thereby decrease its absorption.

The very long terminal half life of doxycycline is nicely demonstrated in the study of Nguyen 1989 where the 36 and 48 hours values has been performed in contrast to many other pharmacokinetic studies of doxycycline.

Doxycycline is lipophilic and is widely distributed in the tissues. High concentrations are found in renal tissue and gallbladder/bile. Therapeutic and relatively higher concentrations than those of ampicillin are-found in sinus secretions, palatine tonsils, nasal polyps and lung tissue (Cunha 1982, Saivin 1988). The Use of doxycycline in upper respiratory tract infections is therefore rational.

Doxycycline is not metabolised in humans (Saivin 1988). It is mainly excreted in faeces and approximately 20% can be recovered in urine. The doxycycline excreted in faeces is probably bound in a way that makes it inactive, as the intestinal flora is not affected by doxycycline treatment (Cunha 1982).

Doxycycline is generally reported to be well tolerated (Cunha 1982).

Doxycycline was first introduced into clinical practice in 1968 as the HCl salt, called doxycycline hyclate. This salt was formulated in tablets or capsules. However, it was soon shown that these formulations had serious side effects. In a study of adverse drug reactions from antibiotics, 35/113 (31%) of patients treated with doxycycline hyclate after questioning reported nausea and vomiting while 24/373 (6.4%) spontaneously reported nausea and vomiting. These frequencies where 3-fold higher than those reported with other antibiotics. The tendency of nausea and vomiting is probably elicited from the stomach.

Another side effect of doxycycline hyclate is esophageal ulceration, if the capsules for some reason do not reach the stomach but remain in the oesophagus.

A solution to these problems has been attempted by the introduction of doxycycline hydrate (base). This new formulation has eliminated the above mentioned side effects, but it soon became apparent that the bioavailability in a number of patients, which were also in treatment with antacids and the like, was significantly reduced.

This can be explained by the lack of acid production in the stomach being the cause of reduced dissolution of doxycycline hydrate.

Considering that a great deal of the population has elevated gastric pH caused by either achlorhydria or due to the intake of antacids, H2-blockers, omeprazazole or the like, antibiotic treatment with doxycycline hydrate gives an unacceptable low bioavailability.

One solution to this problem has recently been suggested by the introduction of doxycycline carrageenate, which has a satisfactory bioavailability in subjects with elevated gastric pH. In subjects with normal pH conditions in the stomach, the use of doxycycline carrageenate has no advantages due to the spontaneous cleavage of doxycycline carrageenate into doxycycline H and carrageenate ion.

A study of cats (EP 091 409) showed that doxycycline carrageenate does not result in oesophagus ulcerations. No human safety data has been found on doxycycline carrageenate. To the best of our knowledge, no or very few clinical studies have been performed with doxycycline carrageenate and therefore a specific side effect profile of this doxycycline salt is not available.

By using different pharmaceutical preparations of doxycycline, attempts have been made to achieve a controlled release effect.

One solution to the aforementioned problems is the use of film coated tablets. A formulation with doxycycline hyclate was developed with less tendency to disintegration in the oesophagus (Delphre 1989). An enteric coated pellet formulation of doxycycline (Doryx®, Doxylets®) has been developed to prevent the total dose of doxycycline hyclate dissolving in a small area of the stomach. Such formulations have been shown to have a reduced (approximately 50% reduction) rate of nausea and vomiting (Khouzam 1987, Berger 1988, Story 1991) and an unchanged bioavailability (Williams 1990). A pellet formulation does not have an automatically unchanged bioavailability. In a doxycycline pellet formulation developed at the University of Nanking, China it was found that 200 mg of the pellet formulation were bioequvivalent to 100 mg of the standard doxycycline hyclate formulation (Qiu 1986).

Therefore, a need exists for a doxycycline formulation with controlled release properties.

The tetracyclines belong to a group of antibiotics which are manufactured by fermentation of various Streptomyces species. The most widely used are doxycycline, oxytetracycline, chlorotetracyclines and tetracycline. A number of semisynthetic tetracycline are known, for instance methacycline and minocycline. The most widespread of these semisynthetic tetracyclines is α-deoxy-5-hydroxy-tetracycline (doxycycline), which is manufactured by a 3-step synthesis with oxytetracycline as the starting material as described in U.S. Pat. No. 3,200,149 to Pfizer (1965). In this patent, the hydrate and the hyclate are also disclosed.

U.S. Pat. No. 3,927,094 to Villax discloses the manufacture of alkali metal polymetaphosphate complexes of doxycycline; This salt is characterized by its high solubility in water.

In GB 2.088.864 to Villax, doxycycline mono-sodium-tetraphosphate is disclosed, which is also very water-soluble and has improved stability.

The sulfosalicylate of doxycycline is known from GB 1,305,860 to Alfa Farmaceutici. This salt is sparingly soluble in water and is used in the doxycycline manufacturing process. The sulfo-salicylic acid salt has no clinical use, as sulfosalicylic acid is not accepted for medicinal use.

In EP 91.409 Kabi Vitrum a complex between doxycycline and carrageenan is disclosed. Carrageenan is a sulphated polysaccharide with a molecular weight from 100,00 to 100,000. This complex is insoluble in water. By dissolution, it is shown that the doxycycline hydrocarrageenate complex releases the active substance at the same rate-as doxycycline hyclate in the gastric juice.

β-D-fructofuranosyl-α-D-glucopyranoside octakis (hydrogen sulphate), referred to in the following as sucrose-octa-O-sulphonic acid, is produced by sulphating sucrose with sulphur trioxide in pyridine. In this process, eight hydroxy groups in sucrose are esterfied with eight molecules of sulphuric acid under the formation of semi-esters. Sucrose-octa-O-sulphonic acid forms well crystallized salts with Na, K, Cs, Rb and ammonium. (Ochi 1980)

Salts of this type are proposed for the treatment or prevention of lesions and/or inflammation of non-peptic ulcer nature in the digestive tract, according to WO 94/00476 to Bukh Meditech.

Thus, the only salt of the sucrose-octa-O-sulphonic acid, which is presently used in medical therapy is the aluminium salt produced by treatment of sucrose-octa-O-sulphonic acid with aluminium hydroxide (U.S. Pat. No. 3,432,489 to Chugai, 1969) and is known under the name sucralfate having the general formula $C_{12}H_{54}Al_{16}O_{75}S_8$, $8H_2O$ (Morikawa, 1981).

Sucralfate is widely used in the treatment of gastric ulcers. Peroral administration of tablets, or a suspension causes sucralfate to react with the acidic gastric juice, under formation of a sticky gel, which adheres to the mucosa and forms a protective layer, especially on the ulcerated areas.

The effect of sucralfate is largely ascribed to the high content of aluminium hydroxide ions which act as acid neutralizers and absorb pepsin and bile salts. (Nagashima, 1981)

No other salts of the sucrose-octa-O-sulphonic acid have hitherto been found suitable for medical purposes.

SUMMARY OF THE INVENTION

It is an object of the invention to provide novel salts of tetracyclines which are well suited for preparation of pharmaceutical compositions for use in medicine.

It has surprisingly been shown that tetracyclines form sparingly soluble salts, or complexes with sucrose-octa-O-sulphonic acid. These compounds are well defined and can be described by the following formula:

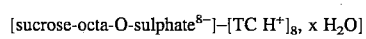

$$[\text{sucrose-octa-O-sulphate}^{8-}]\text{--}[\text{TC H}^+]_8, \text{ x H}_2\text{O}]$$

wherein TC is a tetracycline molecule, and x is a number of from 0 to 20, in which an amount of water forms a hydrate with the new salt or in which water is physically bound to the new salt.

These new salts are sparingly soluble in water and forms well defined crystals.

By the term "tetracyclines" is meant antibiotics of the class containing the following naphthacene-ring system, called tetracyclines.

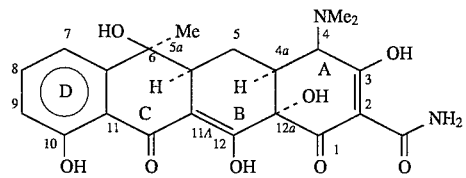

Useful antibiotics of this group consist of tetracycline itself, doxycycline, oxytetracycline, chlorotetracycline, metacycline and minocycline. Especially valuable is doxycycline, which is a 6-deoxy derivative of oxytetracycline with the following chemical name and formula:

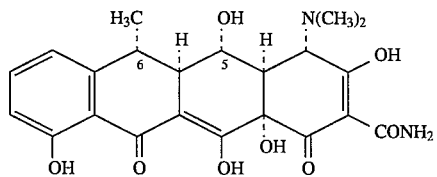

4-dimethylamino-1,4,4a,5,5a,6,11,12a-octahydro-3,5,10,12, 12a-pentahydroxy-6-methyl-1,11-dioxo-2 -naphthacenecarboxamide monohydrate.

The new salts are produced in a manner known per se, e.g. by treating a suspension of a tetracyclines antibiotic in water with an aqueous solution of sucrose-octa-O-sulphonic acid. Particularly preferred is a method where e.g. the doxycycline salt of sucrose-octa-O-sulphonic acid which has the general formula:

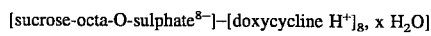

[sucrose-octa-O-sulphate$^{8-}$]–[doxycycline H$^+$]$_8$, x H$_2$O]

hereinafter referred to as doxycycline sucrose octasulphate, is produced by treatment of a solution of doxycycline in hydrochloric acid with an aqueous solution of sucrose-octa-O-sulphonic acid sodium salt.

Due to these reactions, the new salts crystallize as sparingly soluble, well-crystalized salts, which can easily be separated from the reaction mixture by filtration.

DETAILED DESCRIPTION

Doxycycline sucrose octasulphate contains about 70% (10% water). doxycycline and this makes the salt well suited for preparation tablets of a suitable size.

Because of the new salt's low solubility in water, the main part of the active drug will be bound to the sucrose-octa-O-sulphonic acid moiety and thus remain biologically inactive during passage through the oesophagus. This greatly reduces the risk of irritation and ulceration of the mucosa in the oesophagus.

When pharmaceutical formulations are made, which contain the new salt in the form of single doses for oral use, or peroral administration, the salt can be mixed with a solid pulverised carrier, like: Calcium Carbonate, Calcium Phosphates, Calcium, Crospovidone, Sulphate, Mikrocrystalline Cellulose, Cellulose, Dextrates, Dextrin, Dextrose Exipient, Fructose, Lactose, Mannitol, Sorbitol, Starch, Povidone, Pregelatinized Starch, Sucrose, Compressible sugar or Confectioner's Sugar; and can also contain lubricants, like: Calcium Stearate, Magnesium Stearate, Polyethylene Glycol, Stearic Acid, Talc, or Zinc Stearate. The mixture may be prepared and mixed with other subsidiary materials before compressing it into tablets. If coated tablets are desired, then the core—made as outlined above—might be coated with: Sodium Carboxymethyl-cellulose, Cellulose Acetate. Cellulose Acetate Phthalate, Ethylcellulose, Gelatin, Pharmaceutical Glaze, Hydroxypropyl Cellulose, Hydroxypropyl Methylcellulose, Hydroxypropyl Methylcellulose Phthalate, Mothacrylic Acid Copolymer, Methylcellulose, Polyethylene Glycol, Polyvinyl Acetate Phthalate, Shellac, Sucrose, Titanium Dioxide, Carnauba Wax, Microcrystalline Wax or Zein which is first dissolved in a water dissolution, organic dissolution, or a mixture of dissolutions. Colouring agents can be added to this dissolution, so that tablets with different strengths can be identified.

Pulvers and granulata can be made, which contain the new salt alone or can be mixed with a solid pulverised carrier, like: Calcium Carbonate, Calcium Phosphates , Calcium Crospovidone, Sulphate, Microcrystalline Cellulose, Cellulose, Dextrates, Dextrin, Dextrose Exipient, Fructose, Lactose, Mannitol, Sorbitol, Starch, Povidone, Pregelatinized Starch, Sucrose, Compressible sugar, or Confectioner's Sugar; and can also contain lubricants, like: Calcium Stearate, Magnesium Stearate, Polyethylene Glycol, Stearic Acid, Talc, or Zinc Stearate. The remainder can be comprised of, for e.g. sweetening agents, such as sugar, aspartame, dextrates, dextrose, fructose, mannitol, saccharin, calcium saccharin, sodium saccharin, sorbitol or sucrose.

The pulvers or granulate may be dissolved and/or dispersed before use. In the same way, it might be dispersed onto food before administration.

Soft gelatin capsules can be made, which contain a mixture of the salt and/or vegetable oil. Hard gelatin capsules can contain granulates of the complex in combination with a solid pulverised carrier like: Calcium Carbonate, Calcium Phosphates, Calcium, Crospovidone, Sulphate, Microcrystalline Cellulose, Cellulose, Dextrates, Dextrin, Dextrose Exipient, Fructose, Lactose, Mannitol, Sorbitol, Starch, Povidone, Pregelatinized Starch, Sucrose, Compressible sugar, or Confectioner's Sugar, or the new salt alone; and can also contain lubricants, like: Calcium Stearate, Magnesium Stearate, Polyethylene Glycol, Steric Acid, Talc, or Zinc Stearate.

Liquid formulations which may be used in oral use, or peroral administration may be made in the form of syrups, suspensions, emulsions, or mixtures which can contain up to approximately 20% of the new salt. The remainder can be comprised of, for e.g. sweetening agents, such as sugar, aspartame, dextrates, dextrose, fructose, mannitol, saccharin, calcium saccharin, sodium saccharin, sorbitol or sucrose and a mixture of diluents, like ethanol., water, glycerol and propylene glycol.

This dose, which the new salt can administer internally, is dependent on different factors, like for example the individual needs of each patient and-administration's preferences. The dose will be on the same level as normally used for doxycycline, which generally ranges from 100–400 mg/day.

The dissolution properties of the doxycycline sucrose octasulphate according to the invention can easily be demonstrated by the method described in example 6. It is surprising that the new salts have the same dissolution properties as known formulations, in which doxycycline is bound to polymers with high molecular weight, as for instance carrageen.

By modifying the composition of the new salts according to the invention, it is possible to change the dissolution properties in order to optimize the compositions with regard to the dissolution profile desired.

The new salts according to the present invention can also be used locally on the skin, or mucous membranes formulated as creams, lotions, ointments or gels. As an example, doxycycline sucrose octasulphate is well suited for insertion into or around the periodontal pocket of an individual suffering from perodontitis. In this case, the vehicle of the Dumex' patent U.S. Pat. No. 5,143,934 is especially advantageous to use as a carrier.

The invention further relates to the use of a salt of sucrose-octa-O-sulfonic acid and a tetracycline, preferably doxycycline, for the preparation of a medicament.

BRIEF DESCRIPTION OF THE DRAWINGS

The invention is further described by reference to the accompanying drawings in which.

The following examples will illustrate the preparation of the new salts of the invention.

EXAMPLE 1

Sucrose-octa-O-sulphonic acid 65 g of sucrose-octa-O-sulphonic acid sodium salt (produced in accordance with J. Chem. Soc. Faraday Trans., 1981, 77, p. 629–639) are dissolved in 200 ml of water and cation exchanged on Amberlite® IR ($H^+$). The combined solutions are diluted to 1 liter corresponding to an 0.05M solution.

EXAMPLE 2

18.5 g (40 mmol) doxycycline monohydrate is dissolved in 400 ml 0.1M HCl and by addition of 6.5 g (5 mmol), sucrose-octa-O-sulphonic acid-$Na_8$, 8 aq., dissolved in 300 ml water, precipitation of doxycycline sucrose octasulphate takes place. The reaction mixture is stirred for −60 min. at 25° C., filtered, washed with 3×50 water by dispersion and refiltration and vacuum dried at −1 Torr/25C/sicapent®/20 h.

Yield: 23,5 g

Figure 1:
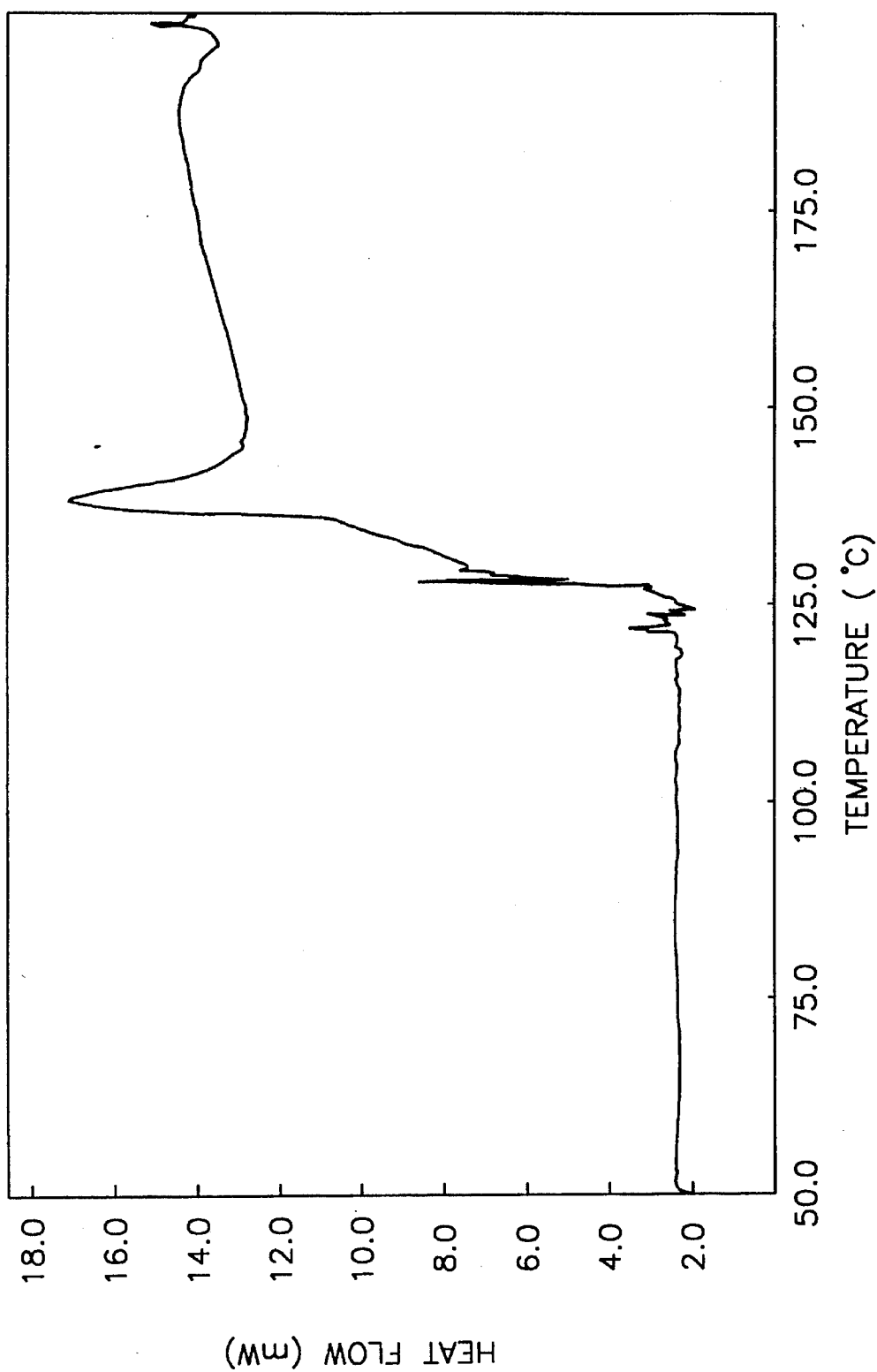
FIG. 1 shows a DSC scan for doxycycline sucrose octasulphate showing a characteristic endothermic peak at about 130° C.

DSC: (FIG. 1) Doxycycline sucrose octasulphate shows a characteristic endoterm peak at about 130° C. The substance does not have a welldefined melting point, but starts to decompose at about 150° C.

Stoichiometric proportions: In the batches produced, the content of water was found to be about 10%. The content of doxycycline was found to be about 77%, calculated with reference to the dried substance. This content of doxycycline indicates that 8moles of doxycycline complexes with 1 mole of sucrose-octa-O-sulphonic acid.

Figure 2:
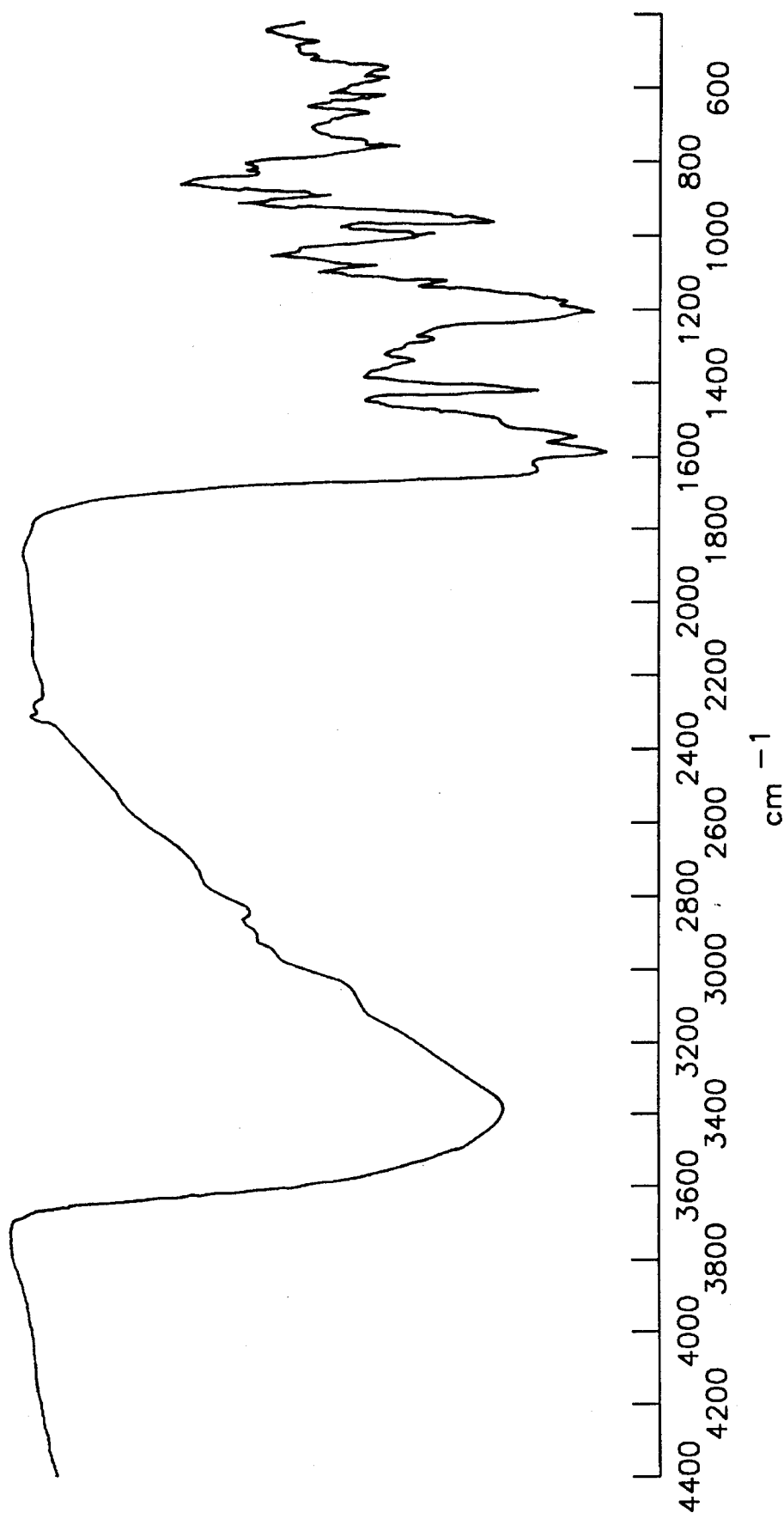
FIG. 2 shows the infrared spectrum of doxycycline sucrose octasulphate.
Figure 3:
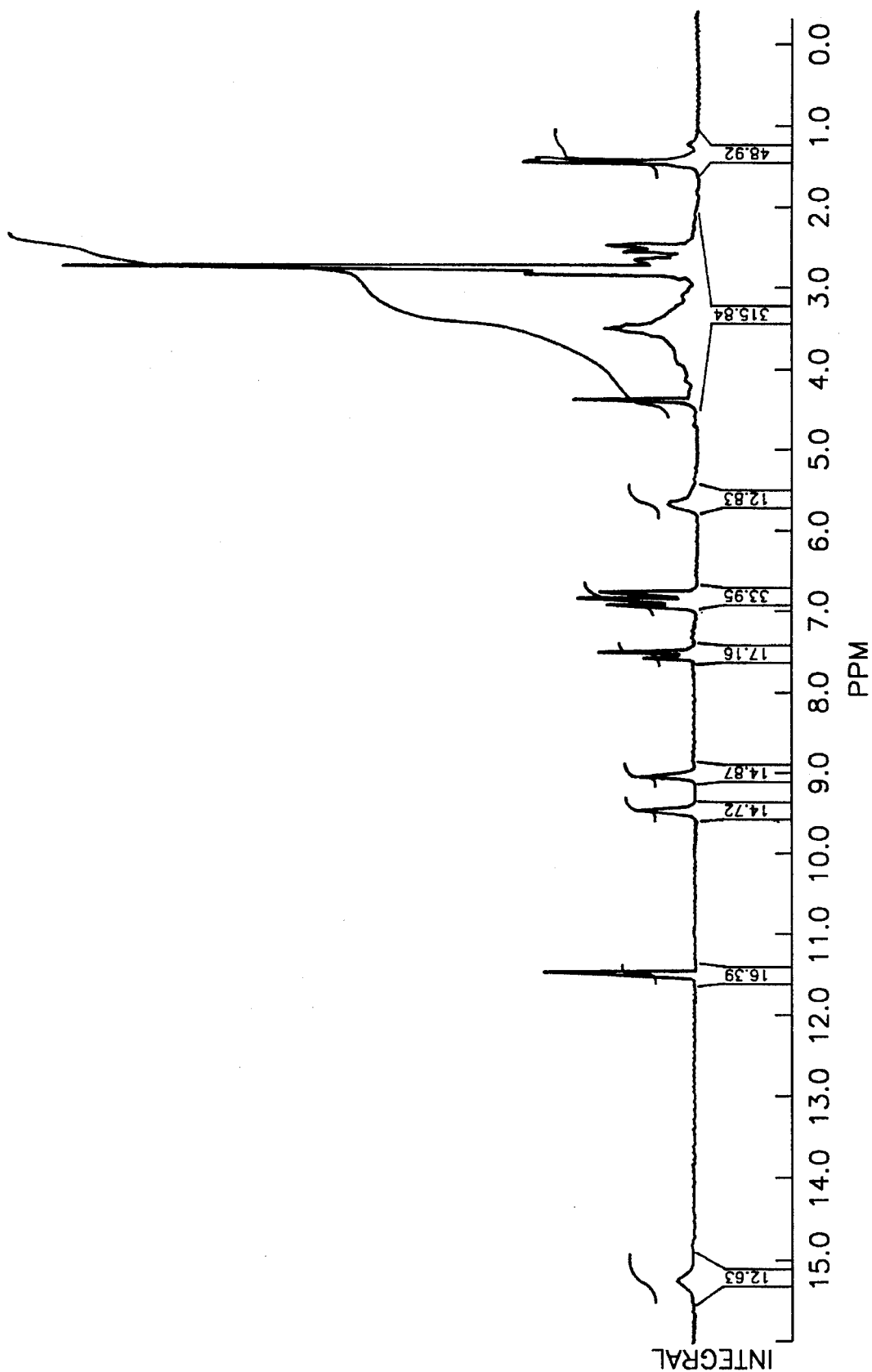
FIG. 3 shows the NMR spectrum of doxycycline sucrose octasulphate.

The IR and NMR spectra for doxycycline sucrose octasulphate are shown in FIGS. 2 and 3.

Characteristics of the IR spectrum (KBr disk) are as follows:

| Group Moiety | Band at wavenumber ($cm^{-1}$) |
| --- | --- |
| —O—H stretch | 3000–3700 |
| aliphatic stretch | 2800–3000 |
| water | 1640 |
| —O—H bend | about 1440 |
| aliphatic bend | 1300–1440 |
| R—O—$SO_3$ asymmetric stretch | 1200–1300 |
| R—O—$SO_3$ asymmetric bend | about 600 |
| C—O stretch | 1000–1100 |

The characteristics of the $^1$H-NMR spectrum (DMSO) are as follows:

Signal originating from doxycycline;

| Proton | δ (ppm) |
| --- | --- |
| $(R)_2$—CH—OH | 4.4 singlet |
| $(R)_2$—CH—C$\underline{H}_3$ (6H) | 1.5 one singlet |
| R—C$\underline{H}$—R (5H) | 2.4–2.6 complex |
| N(C$\underline{H}_3$)$_2$ | 2.8 singlet |
| water | 3.5 complex |
| Ar—$\underline{H}$(o, p) | 6.8–7.0 two doublets |

| Proton | δ (ppm) |
| --- | --- |
| Ar—$\underline{H}$(m) | 7.5 one triplet |
| C=C—OH | 9.0 and 9.5 singlets |
| Ar—O$\underline{H}$ | 11.5 one singlet |
| CON$\underline{H}_2$ | 15.2 one singlet (broad) |

Signals originating from sucrose-octa-O-sulfonic acid;

| Proton | δ (ppm) |
| --- | --- |
| $(R)_2$—CH—O and R—C$\underline{H}_2$O and R—C$\underline{H}$(O)$_2$ | 3.0–4.8 complex |

EXAMPLE 3

20.5 g doxycycline hyclate (40 mmol) is dissolved in 400 ml water and with vigorous stirring, 100 ml of the acid solution of example 1 is added. After 30 min, the pH is adjusted to 3.5 by 0.1M NaOH-solution. After another 30 min. of stirring, the precipitate is filtered and dried as in e.g. example 2.

EXAMPLE 4

18.5 g (40 mmol) doxycycline monohydrate is dissolved in 400 ml 0.1M HCl and by titration with 100 ml 0.05M (5 mmol) sucrose-octa-O-sulphonic acid precipitation of doxycycline sucrose octasulphate takes place. The reaction mixture is stirred for −60 min. at 25C, filtered, washed with 3×50 ml water (by dispersion and refiltration) and vacuum dried at −1 Torr/25° C./sicapent®/20h.

EXAMPLE 5

By titration of 6.5 g (5 mmol) sucrose-octa-O-sulphonic acid $Na_8$, 8 aq. dissolved in 300 ml water, with 18.5 g (40 mmol) doxycycline monohydrate dissolved in 400 ml 0.1M HCl, precipitation of doxycycline sucrose octasulphate takes place. The reaction mixture is stirred for −60 min. at 25° C., filtered, washed with 3×50 ml water (by dispersion and refiltration) and vacuum dried at −1 Tort/25C/sicapente®/ 20h.

EXAMPLE 6

Dissolution of doxycycline sucrose octasulphate:

The paddle method is used in accordance with USP XXII, p. 1579, (apparatus II), with 900 ml 0.1N HCl. One tablet containing 150, mg doxycycline sucrose octasulphate (equal to 105 mg doxycycline) is placed in the dissolution apparatus. Samples are taken after 5, 10, 20, 30, and 60 minutes and diluted.

The samples are analyzed spectrophotometrically at 345.9 nm in a Shimatzu 160 A photometer.

The results are compared to samples of Vibramycin® from Pfizer, which contains doxycycline carrageenate.

Figure 4:
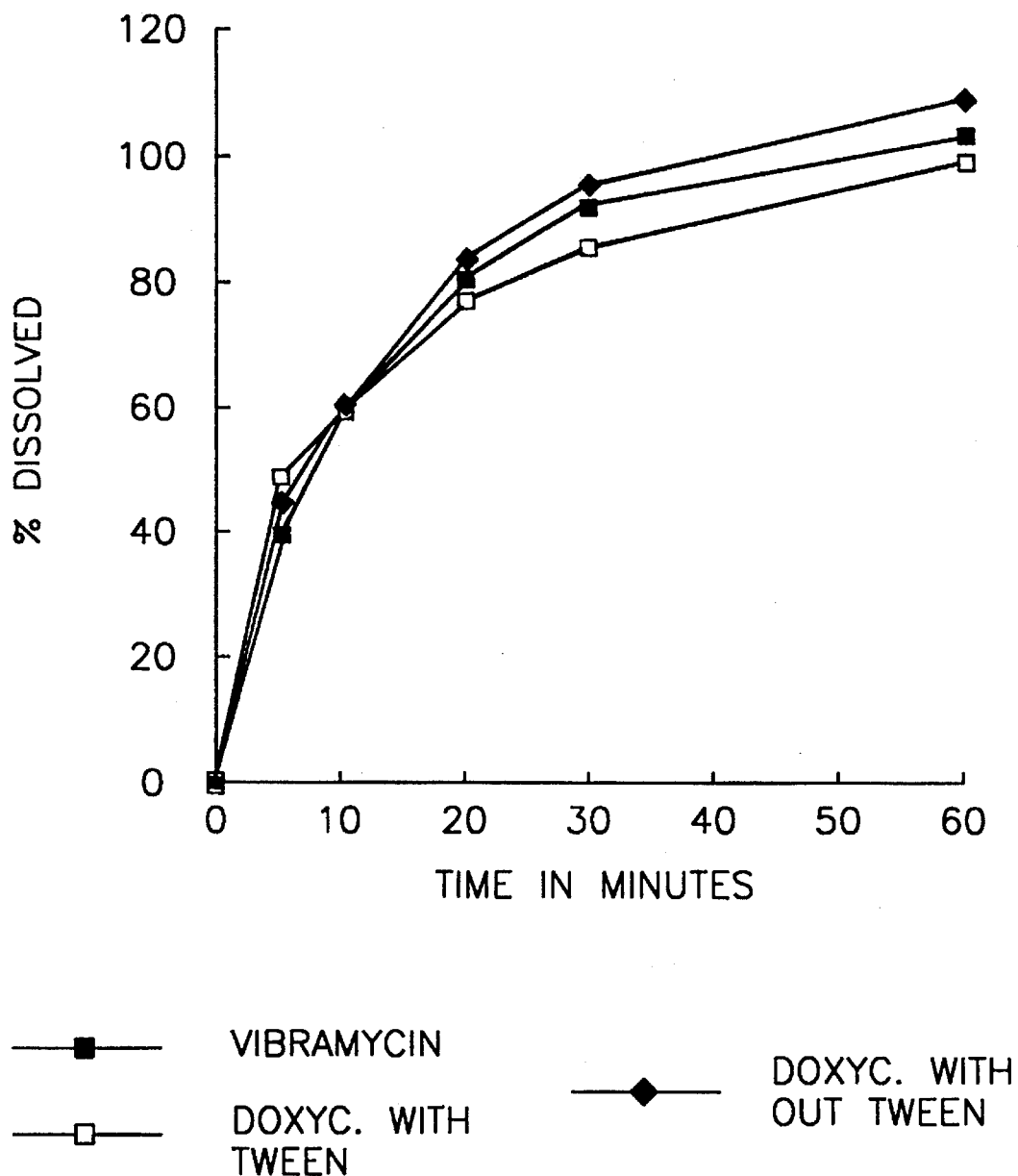
FIG. 4 shows a plot of the percentage release of antibiotic against time for three 100 mg tablets, the first containing vibramycin, the second containing doxycycline sucrose octasulphate salt and Tween and the third containing doxycycline sucrose octasulphate salt without Tween.

The data represented in FIG. 4, which shows a plot of the percentages of release over time, is set out in Table I below:

TABLE I

Comparison of Vibramycin and Doxycycline SOS tablets 100 mg

| Time (minutes) | Vibramycin | Doxycycline-SOS with Tween | Doxycycline-SOS without Tween |
|---|---|---|---|
| 0 | 0 | 0 | 0 |
| 5 | 37.45 | 45.89 | 42.02 |
| 10 | 56.06 | 56.12 | 57.22 |
| 20 | 76.75 | 73.31 | 79.54 |
| 30 | 88.08 | 81.42 | 91.06 |
| 60 | 98.67 | 94.76 | 104.29 |

It will be understood that while specific embodiments of the present invention have been described above others may practice the invention in any of the numerous ways which are suggested to one skilled in the art, by this disclosure. Thus, all such practice of the invention are considered to be a part hereof which fall within the scope of the appended claims.

REFERENCES

Berger RS (1988) A double-blind, multiple-dose, placebo-controlled, Cross-over study to compare the incidence of gastrointestinal complaints in healthy subjects given Doryx R and Vibramycin R. J Clin Pharmacol 28, 367–370.

Bogardus JB, Blackwood RK (1979) Dissolution rates of doxycycline free base and hydrochloride salts. J Pharm Sciences 68, 1183–1184.

Cunha BA, Sibley CM, Ristuccia AM (1982) Doxycycline. Therapeutic drug Monitoring 4, 115–135.

Delphre G, Kadish U, Stahl B (1989) Induction of esophageal injuries by doxycycline and other pills. Digestive diseases and Sciences 34, 797–800.

Gibaldi M (1967) Pharmacokinetics of absorption and elimination of doxycycline in man. Chemoterapia 12, 265–271.

Grahnén A, Lönnebo A, Eckernäs S-Å (1991) Effect of increasing gastric pH on the relative bioavailability of doxycycline carrageenate tablets 100 mg (kabi Pharmacia) in comparison. Internal study report, PCB, Sweden.

Khouzam S, Yazbeck D (1987) Étude comparative de la tolérance gastrique de l' hyclate de doxycycline après administration orales uniques croisées de deux formulations. Acta Therapeutica 3, 309–315.

Maltaborg A-S (1984) Bioavalability of Doxycycline Monohydrate. A comparison with equivalent doses of doxycycline hydrochloride. Chemotherapy 30, 76–80.

Morikawa, Hideki et. al. (1981) Structural analysis of the amorphous sodium salt of Aluminium Hydroxide salt of Sucrose Octasulfate. J. Chem. Soc. Faraday Trans. 1, 77, 629–639.

Nagashima, Renpei, (1981) Macanisms of action of sucralfate. Clin. Gastroenterol. 3, suppl. 2, pp. 117–127.

Nguyen VX, Nix DE, Gillikin S, Schentag JJ (1989) Effect of oral antacid administration on the pharmacokinetics of intravenous doxycycline. Antimicrob. Agents Chemother. 33, 434–436.

Ochi, Kiyoshige et. al. (1980) Crystalline salts of Sucrose Octasulfate. chem. Pharm. Bull. 28 (2), 638–641.

Qiu Y-H, Tu X-D, Mao F-F (1986) Development and pharmacokinetic study of sustained release doxycycline hydrochloride pellets. Acta Pharmaceutic Sinica 21, 370–376.

Saivin S, Houin G (1988) Clinical pharmakokinetics of doxycycline and minocycline. Clinical Pharmakokinetics 15, 355–366.

Schach von Wittenau M (1974) Pharmacokinetics of Doxycycline. Opuscula Medica 53 (Suppl. 23) 5–10.

Story MJ, McCloud PI, Boehm G (1991) Doxycycline tolerance study. Incidence of nausea after doxycycline administration to healthy volunteers: A comparison of 2 formulations (Doryx' vs Vibramycin'). Eur J Clin Pharmacol 40, 419–421.

Williams DB, O'Reilly WJ, Boehm G, Story MJ (1990) Absorption of doxycycline from a controlled release pellet formulation: The influence of food on bioavailability. Biopharmaceutics & Drug disposition 11, 93–105.

U.S. Pat. No. 3.200.149 to Pfizer.
U.S. Pat. No. 3.432.489 to Chugai.
U.S. Pat. No. 3.927.094 to Villax.
GB 2.088.864 to Villax.
EP 091.409 to Kabi Vitrum.
U.S. Pat. No. 5.143.934 to Dumex.
PCT WO 94/00476 to Bukh Meditech.

We claim:

1. A salt of sucrose-octa-O-sulfonic acid and a tetracycline.

2. A salt according to claim 1 which has the formula $$[\text{sucrose-octa-O-sulfonate}^{8-}][\text{TC H}^+]_8, x\ H_2O$$

in which "TC" means a tetracycline and x means a number of from 0 to 20.

3. A salt according to claim 2, wherein "TC" is selected from the group consisting of doxycycline, tetracycline, oxytetracycline, chlorotetracycline, metacycline and minocycline.

4. A salt according to claim 3, wherein "TC" is doxycycline.

5. A pharmaceutical composition comprising the salt according to claim 1 and a pharmaceutically acceptable excipient.

6. A pharmaceutical composition according to claim 5 which comprises at least one unit dosage form selected from the group consisting of a tablet, a capsule formulation, a liquid formulation and combinations thereof.

7. A method of treating diseases in a warm-blooded animal by inhibiting protein synthesis of bacteria causing such diseases comprising administering to said warm-blooded animal a bacterial protein synthesis inhibiting effective amount of the pharmaceutical composition of claim 5.

8. The method of claim 7 wherein said effective amount is from 100 to 400 mg/day.

9. The method of claim 7 wherein a tetracycline is selected from the group consisting of doxycycline, tetracycline, oxytetracycline, chlorotetracycline, metacycline and minocycline.

10. The method of claim 9 wherein a tetracycline is doxycycline.

11. The method of claim 7 comprising administering the pharmaceutical composition orally, perorally or topically.

12. The pharmaceutical composition of claim 5 wherein a tetracycline is selected from the group consisting of doxycycline, tetracycline, oxytetracycline, chlorotetracycline, metacycline and minocycline.

13. The pharmaceutical composition of claim 12 wherein a tetracycline is doxycycline.

14. The pharmaceutical composition of claim 6 in which the unit dosage form is suitable for oral administration.

15. The pharmaceutical composition of claim 5 in which the pharmaceutically acceptable excipient is selected from the group consisting of carriers, lubricants, coloring agents and mixtures thereof.

* * * * *